US009101428B2

(12) United States Patent
Long et al.

(10) Patent No.: US 9,101,428 B2
(45) Date of Patent: Aug. 11, 2015

(54) MODULAR BONE PLATE SYSTEM

(71) Applicant: Biomet C.V., Gibraltar (GI)

(72) Inventors: Jack F. Long, Warsaw, IN (US); Kelly R. Marbaugh, Celina, OH (US); Bart R. Huffman, Silver Lake, IN (US)

(73) Assignee: Biomet C.V., Gibraltar (GI)

( * ) Notice: Subject to any disclaimer, the term of this patent is extended or adjusted under 35 U.S.C. 154(b) by 243 days.

(21) Appl. No.: 13/689,807

(22) Filed: Nov. 30, 2012

(65) Prior Publication Data

US 2013/0086789 A1 Apr. 11, 2013

Related U.S. Application Data

(62) Division of application No. 11/904,078, filed on Sep. 26, 2007, now Pat. No. 8,343,154.

(51) Int. Cl.
*A61B 17/88* (2006.01)
*A61B 17/80* (2006.01)

(52) U.S. Cl.
CPC .............. *A61B 17/88* (2013.01); *A61B 17/80* (2013.01); *A61B 17/8052* (2013.01); *A61B 17/8057* (2013.01); *A61B 17/8085* (2013.01)

(58) Field of Classification Search
CPC .............. A61B 17/80; A61B 17/8052; A61B 17/8057; A61B 17/8085; A61B 17/88
USPC .............. 29/428, 446, 453; 59/82, 84–93, 95; 474/206; 606/70–71, 151–158, 606/280–299, 902–906
See application file for complete search history.

(56) References Cited

U.S. PATENT DOCUMENTS

| | | | |
|---|---|---|---|
| 2,406,832 A | 9/1946 | Hardinge |
| 4,272,952 A | 6/1981 | Graham |
| 4,625,507 A | 12/1986 | Moritz et al. |
| 5,527,310 A | 6/1996 | Cole et al. |
| 5,766,175 A | 6/1998 | Martinotti |
| 5,800,162 A | 9/1998 | Shimodaira et al. |
| 5,879,352 A | 3/1999 | Filoso et al. |
| 5,975,904 A | 11/1999 | Spiegel |

(Continued)

FOREIGN PATENT DOCUMENTS

| | | | |
|---|---|---|---|
| DE | 19834326 A1 | 2/2000 | |
| DE | 102006062164 A1 * | 6/2008 | ............. A61B 17/80 |

(Continued)

OTHER PUBLICATIONS

Translation of DE 10 2006 062 164; Wolter, Dietmar; Obtained from EPO website <http://worldwide.espacenet.com/publicationDetails/biblio?DB=worldwide.espacenet.com&II=0&ND=3&adjacent=true&locale=en_EP&FT=D&date=20090923&CC=EP&NR=2101666A1&KC=A1> on Jan. 29, 2015.*

(Continued)

*Primary Examiner* — Larry E Waggle, Jr.
(74) *Attorney, Agent, or Firm* — Harness, Dickey

(57) ABSTRACT

A modular bone plating system in one embodiment is a bone plate kit including a plurality of bone plates, each of the plurality of bone plates including a male coupling portion, a female coupling portion and a shaft extending between the male coupling portion and the female coupling portion, wherein each of the male coupling portions of each of the plurality of bone plates is configured to couple with each of the female coupling portions of each of the other of the plurality of bone plates.

22 Claims, 7 Drawing Sheets

(56) References Cited

U.S. PATENT DOCUMENTS

| | | | |
|---|---|---|---|
| 6,340,362 B1 | 1/2002 | Pierer et al. | |
| 6,524,315 B1 | 2/2003 | Selvitelli et al. | |
| 6,547,790 B2 | 4/2003 | Harkey, III et al. | |
| 6,666,873 B1 | 12/2003 | Cassell | |
| 7,112,202 B2 | 9/2006 | Michelson | |
| 7,621,914 B2* | 11/2009 | Ralph et al. | 606/71 |
| 7,628,816 B2 | 12/2009 | Magerl et al. | |
| 2002/0128653 A1 | 9/2002 | Haidukewych | |
| 2004/0102777 A1 | 5/2004 | Huebner | |
| 2004/0102778 A1 | 5/2004 | Huebner et al. | |
| 2004/0102779 A1 | 5/2004 | Nesper et al. | |
| 2004/0167521 A1* | 8/2004 | De Windt | 606/69 |
| 2005/0010227 A1* | 1/2005 | Paul | 606/71 |
| 2005/0107796 A1* | 5/2005 | Gerlach et al. | 606/69 |
| 2005/0137597 A1 | 6/2005 | Butler et al. | |
| 2005/0149026 A1 | 7/2005 | Butler et al. | |
| 2005/0240185 A1 | 10/2005 | Boomer et al. | |
| 2006/0079892 A1 | 4/2006 | Roychowdhury et al. | |
| 2006/0116683 A1* | 6/2006 | Barrall et al. | 606/71 |
| 2006/0229610 A1 | 10/2006 | Piehl | |
| 2006/0271052 A1* | 11/2006 | Stern | 606/69 |
| 2006/0276794 A1 | 12/2006 | Stern | |
| 2008/0097432 A1 | 4/2008 | Schulze | |

FOREIGN PATENT DOCUMENTS

| | | |
|---|---|---|
| WO | WO-2006050400 A2 | 5/2006 |
| WO | WO-2006060506 A1 | 6/2006 |

OTHER PUBLICATIONS

International search report in a corresponding PCT application (i.e. PCT/US2008/076963), dated Jan. 8, 2009 (6 pages).

* cited by examiner

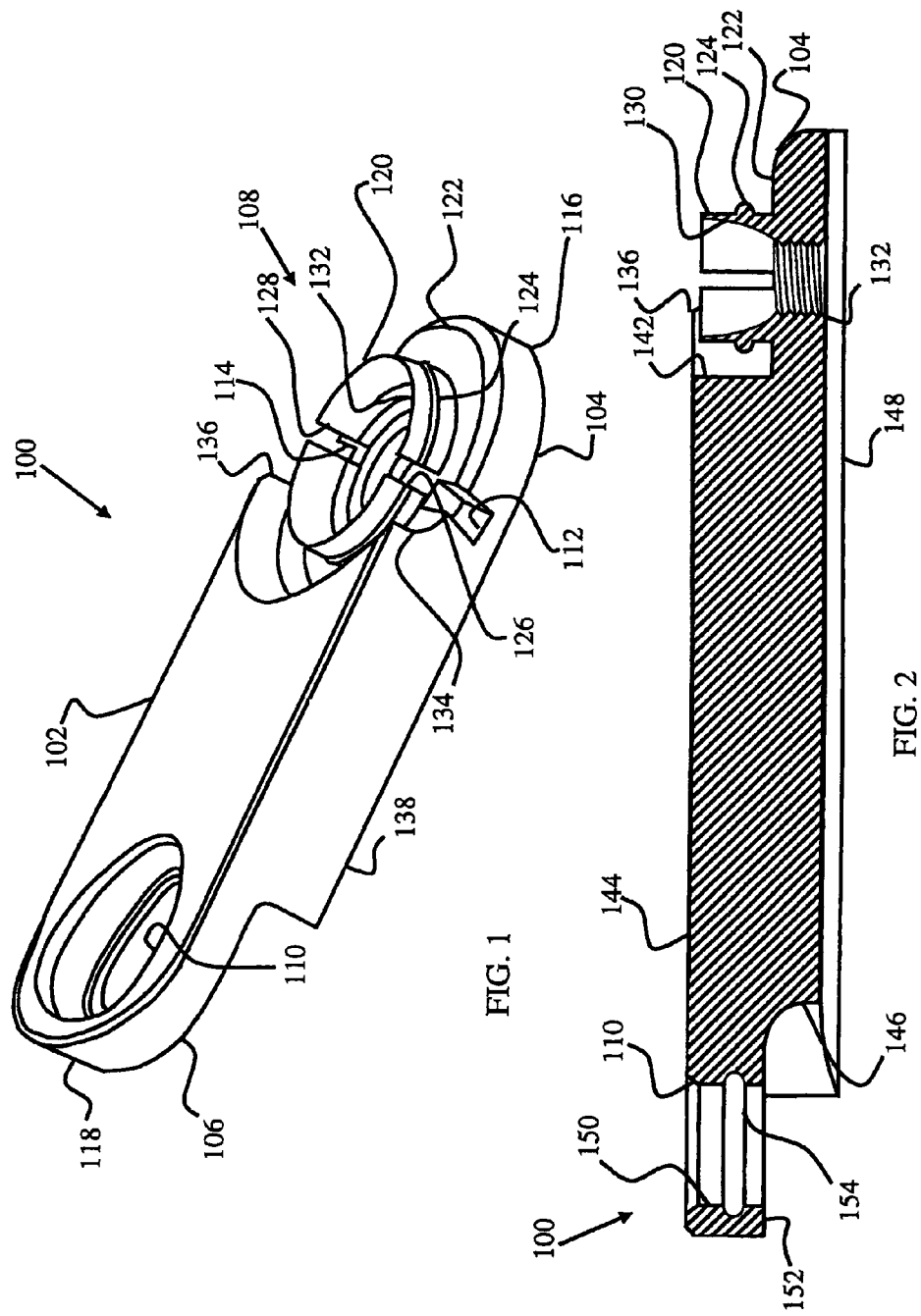

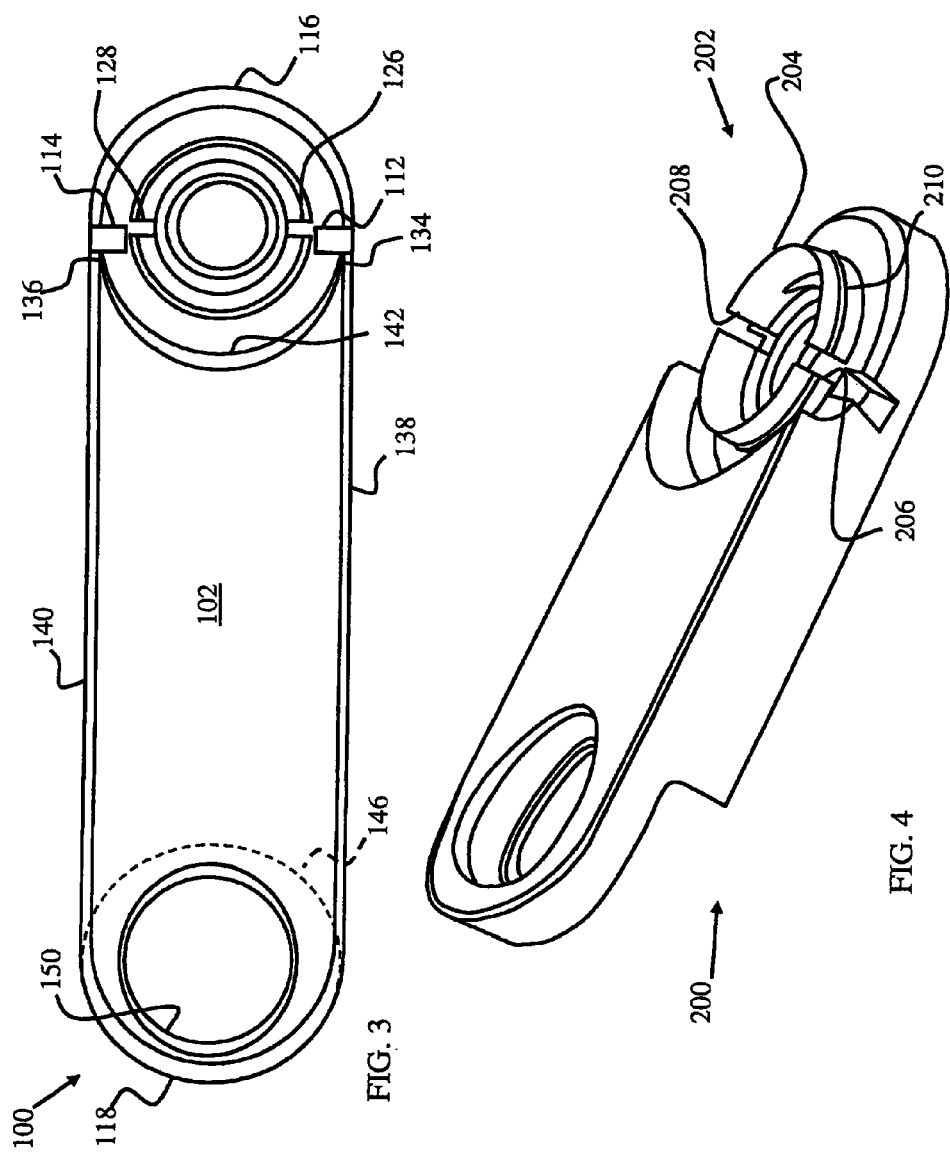

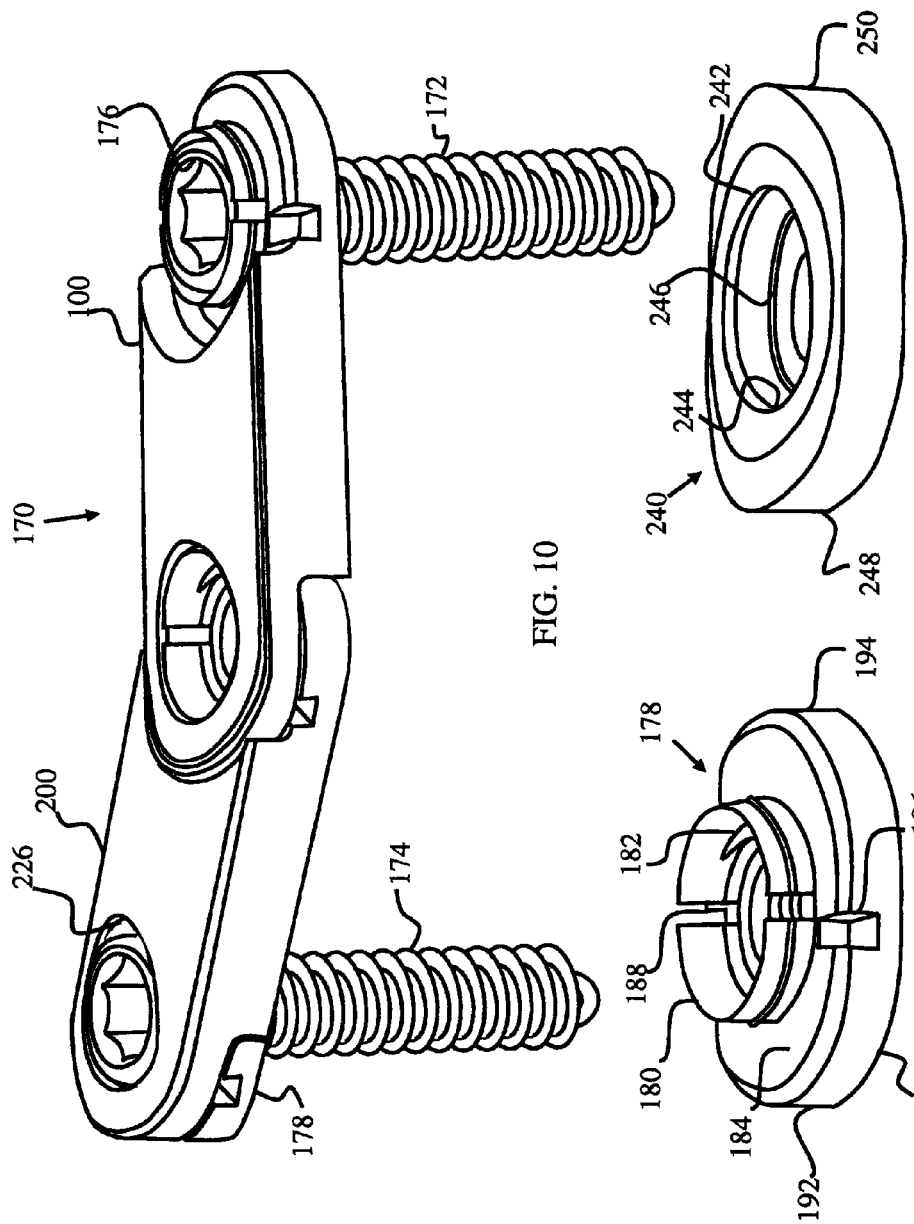

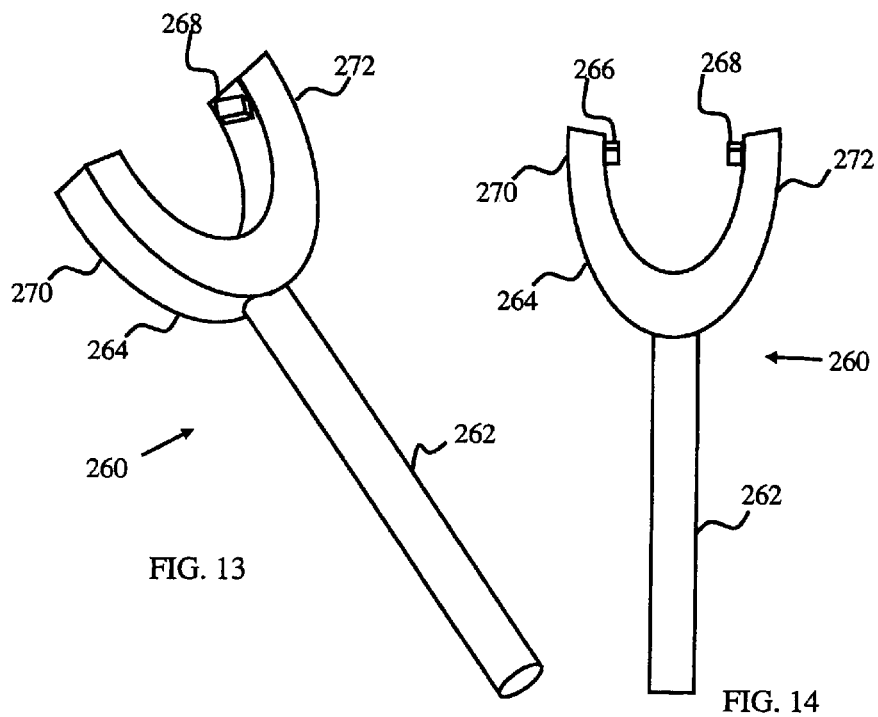
FIG. 13
FIG. 14
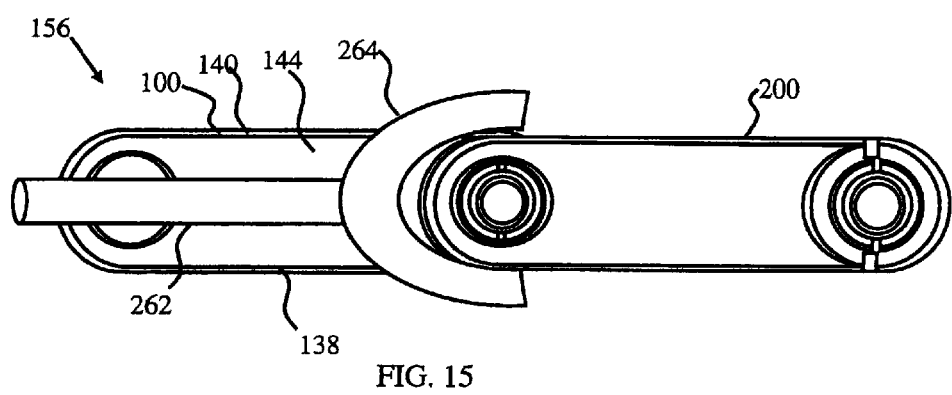
FIG. 15

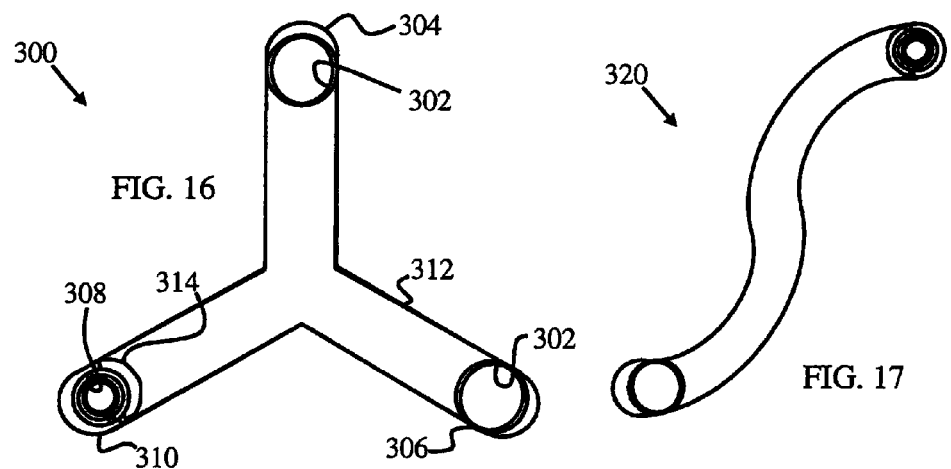
FIG. 16
FIG. 17
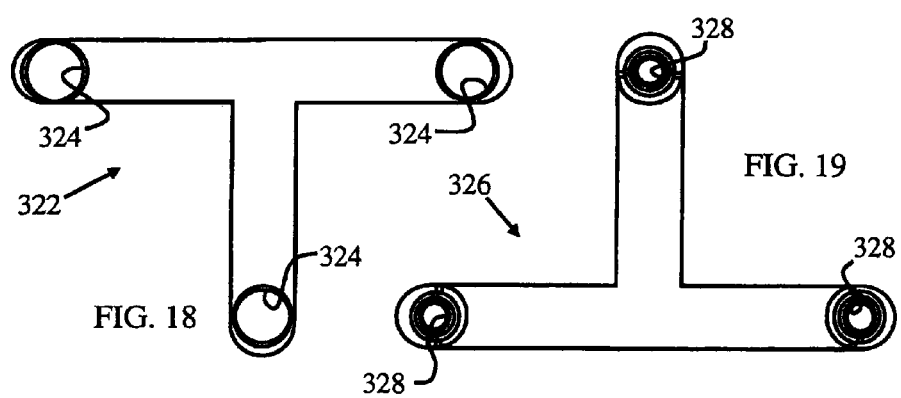
FIG. 18
FIG. 19
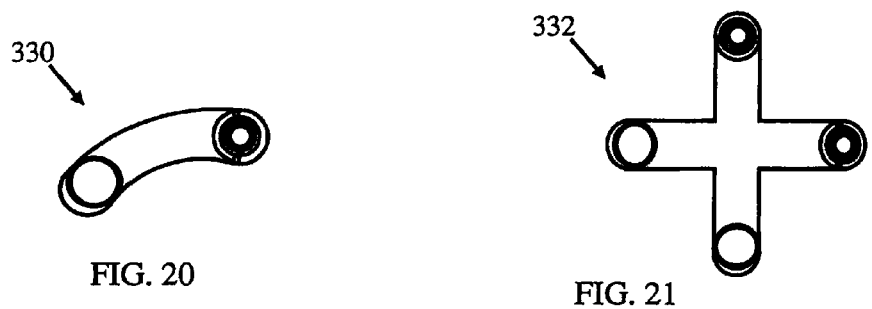
FIG. 20
FIG. 21

MODULAR BONE PLATE SYSTEM

CROSS REFERENCE TO RELATED APPLICATIONS

This application is a divisional application of U.S. application Ser. No. 11/904,078 filed on Sep. 26, 2007. The disclosure of the above application is incorporated herein by reference.

FIELD OF THE INVENTION

This invention relates to the field of orthopaedics and more particularly to methods and instrumentation used in orthopaedic procedures.

BACKGROUND

A bone plate is a hard, normally metallic plate that is configured for attachment to bone surfaces, across bone fragments or across areas of bone reconstruction. The bone plate is used to provide stability to those areas and may further be used to compress and immobilize those areas so as to facilitate rebuilding and mending of the bones. Typically, a bone plate is an elongated strip with a number of openings located at regular intervals for attachment of the bone plate to a bone using bone screws. The surfaces of the strip may be contoured, textured or otherwise formed to facilitate secure placement on a bone surface.

Some bone plates, such as compression plates, are positioned tightly against the outer surface of the bone. Accordingly, to provide proper distribution of loads between the bone and the bone plate, the bone plate should be closely conformed to the bone contours. The contours of the bones to which bone plates are attached, however, vary from individual to individual. Accordingly, maintaining an inventory of bone plates which are specially formed for an individual or even a group of individuals is cost prohibitive.

One type of bone plate that has been developed in response to problem of providing a bone plate that is properly shaped, is a reconstruction bar. Reconstruction bars are formed from a biocompatible material that can be bent using special tools during a surgery. Typically, the surgeon forms by hand a thin metal template of the specific bone contour at the desired implantation cite. This process is generally performed after an incision has been made to expose the implantation location and the metal template is physically placed against the patient's bone.

Once a template is formed, the surgeon uses the special tools to shape the reconstruction bar to visually match the metal template. A number of tools have been developed to assist in reshaping the bone plates. The tools include are bending irons, specially adapted pliers, and bench-mounted bending presses that will bend a plate between a pair of anvils, one anvil having a single contact point, and the opposite anvil having a spaced pair of contact points. The shaped reconstruction bar is then attached to the bone using bone screws. Therefore, in addition to the expense of the special tools, this process can be time consuming and require a high level of skill to achieve an acceptably shaped bone plate.

Moreover, the shaped bone plate will generally not conform exactly to the surface of the bone at the attachment location. Thus, tightening of the bone plate against the bone with the bone screws induces bending preloads on the bone plate resulting in spring-back due to the resilient properties of the bone plate. Additionally, gaps may be present between the bone plate and the bone resulting in an uneven transfer of load from the plate to the bone. Consequently, the bone screw may break or strip away from the bone resulting in loss of fracture reduction, bone misalignment, extended healing time or corrective surgeries.

Therefore, a need exists for a bone plate that can easily be conformed to the shape of a patient's bone. A further need exists for a bone plate that does not require a large number of special tools and which is easy to manufacture.

SUMMARY

Orthopaedic instrumentation and a method of manufacturing the instrumentation is disclosed. In one embodiment, a modular bone plate includes a male snap-fit coupling portion, a female snap-fit coupling portion, and a shaft extending between the male coupling portion and the female coupling portion, the shaft including a bottom bone contacting surface and an upper surface opposite the bone contacting surface.

In a further embodiment a bone plate kit includes a plurality of bone plates, each of the plurality of bone plates including a male coupling portion, a female coupling portion and a shaft extending between the male coupling portion and the female coupling portion, wherein each of the male coupling portions of each of the plurality of bone plates is configured to couple with each of the female coupling portions of each of the other of the plurality of bone plates.

A method of constructing a bone plate includes aligning a male coupling portion of a first bone plate module with a female coupling portion of a second bone plate module, compressing a taper of the male coupling portion, inserting the compressed taper into the female coupling portion, rigidly coupling the first bone plate module with the second bone plate module, placing the rigidly coupled first bone plate module and second bone plate module on the surface of a bone, inserting a portion of a fastener through the male coupling portion and attaching the rigidly coupled first bone plate module and second bone plate module to the surface of a bone with the fastener

BRIEF DESCRIPTION OF THE DRAWINGS

FIG. 1 depicts a perspective view of a bone plate module with a male coupling portion and a female coupling portion in accordance with principles of the present invention;

FIG. 2 depicts a cross-sectional view of the bone plate module of FIG. 1;

FIG. 3 depicts a top plan view of the bone plate module of FIG. 1 that can be coupled with another bone plate module;

FIG. 4 depicts a perspective view of a bone plate module that can be coupled with the bone plate module of FIG. 1;

FIG. 10 depicts the bone plate modules of FIG. 4 and FIG. 1 rigidly coupled together to form an angled portion of a bone plate with a fastener inserted through the male coupling portion of one bone plate module and another fastener inserted through the female coupling portion of the second bone plate modules and through a male end cap.

FIG. 11 depicts the end cap of FIG. 10;

FIG. 12 depicts a female end cap that may be used with the male coupling portion of the bone plate module of FIG. 1;

FIGS. 13 and 14 show views of a decoupler that may be used to decouple two rigidly coupled bone plate modules;

FIG. 15 depicts the decoupler of FIGS. 13 and 14 positioned along the shaft of the bone plate module shown in FIG. 1 so as to decouple the bone plate modules of FIG. 4 and FIG. 1; and FIGS. 16-21 depict various alternative configurations of bone plate modules with coupling portion in accordance with principles of the present invention.

DETAILED DESCRIPTION

Figure 5:
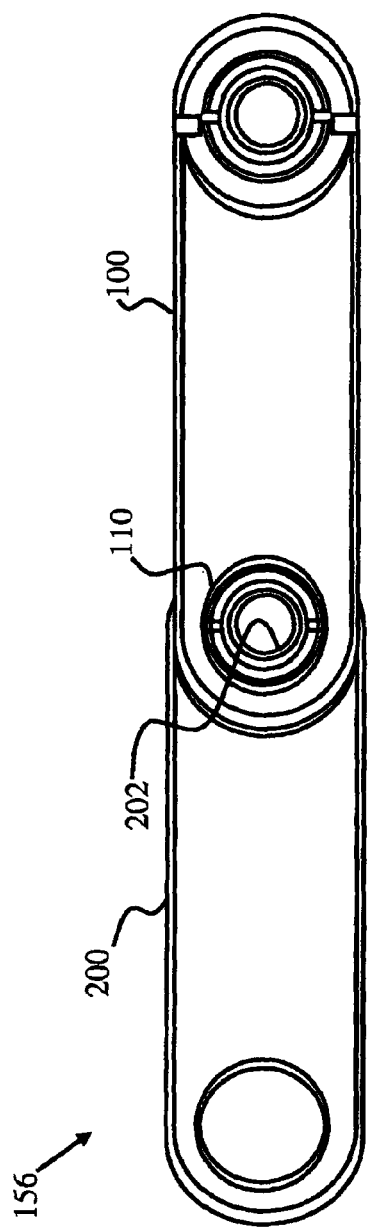
FIG. 5. depicts a top plan view of the bone plate module of FIG. 1 coupled with the bone plate module of FIG. 4 to form a straight portion of a bone plate.

FIG. 1 shows a bone plate module 100. The bone plate module 100 includes a shaft 102 extending between two end portions 104 and 106. A male coupling portion 108 is positioned at the end portion 104 and a female coupling portion 110 is positioned at the end portion 106. Two notches 112 and 114 are located on the end portion 104 next to the male coupling portion 108. The end portion 104 terminates at a curved outer perimeter 116 and the end portion 106 terminates at a curved outer perimeter 118.

The male coupling portion 108 includes a taper 120 which extends upwardly from a plateau 122. A ridge 124 extends around the perimeter of and outwardly from the taper 120. Two slots 126 and 128 are formed in the taper 120 and the ridge 124. The inner surface 130 of the taper 120 curves downwardly and inwardly to a threaded portion 132 as shown in FIG. 2.

Two rotation stops 134 and 136 are located at one end of the shaft 102 near the male coupling portion 108. Referring to FIG. 3, the shaft 102 includes side walls 138 and 140 which extend from the end portion 104 to the end portion 106. An inwardly curved wall 142 is located at the end of the shaft 106 nearest the end portion 104 and extends downwardly from the upper surface 144 of the bone plate module 100. Another inwardly curved wall 146 which is located at the end of the shaft 106 nearest the end portion 106 extends upwardly from the bottom surface 148 of the bone plate module 100.

The female coupling portion 110 includes a bore 150 which extends downwardly from the upper surface 144 and opens to an overhang 152. The overhang 152 is located between the curved wall 146 and the outer perimeter 118. A groove 154 extends about the perimeter of the bore 150.

The bore 150 is sized to be slightly smaller in diameter than the diameter of the taper 120. The groove 154, which is sized complementary to the ridge 124, is located at a distance away from the opening of the bore 150 to the overhang 152 that is about the same as the distance at which the ridge 124 is positioned on the taper 120 above the plateau 122. Additionally, the curvature of the inwardly curved wall 146 is complementary to the curvature of the outer perimeter 116 and the curvature of the inwardly curved wall 142 is complementary to the curvature of the outer perimeter 118.

The complementary configuration of the end portion 104 and the end portion 106 along with the configuration of the male coupling portion 108 and the female coupling portion 110 allow two or more bone plate modules like the bone plate module 100 to be rigidly coupled. By way of example, FIG. 4 shows a bone plate module 200 which is identical to the bone plate module 100 in all respects. The bone plate module 100 and the bone plate module 200 may be rigidly coupled as shown in FIG. 5.

Coupling of the bone plate module 100 with the bone plate module 200 to obtain the bone plate 156 shown in FIG. 5 is accomplished by aligning the male coupling portion 202 of the bone plate module 200 with the female coupling portion 110 of the bone plate module 100. The male coupling portion 202 and the female coupling portion 110 are then pressed together. The diameter of the bore 150 is slightly smaller than the diameter of the taper 204. Accordingly, the taper 204 is placed under a compressive force.

The bone plate module 200 is made from a biocompatible material. Such materials include stainless steel, titanium alloy and polymers. These materials exhibit some amount of flexibility when formed with a thin cross section. Thus, the thin walls of the taper 204, particularly at the upper portion of the taper 204, allow the taper 204 to flex inwardly. Moreover, the slots 206 and 208 allow additional flexure. Depending upon the materials used and the particular design, more, fewer or even no slots may be incorporated.

Inward flexure of the taper 204 allows the taper 204 to slide into the bore 150. As the ridge 210 contacts the opening of the bore 150 to the overlap 152, additional force is required to flex the taper 204 farther in the inward direction so that the ridge 210 can enter into the bore 150. As the taper 204 is inserted more fully into the bore 150, the ridge 210 aligns with the groove 154. The increased diameter of the groove 154 compared to the remainder of the bore 150 allows the taper 204 to flex outwardly, thereby forcing the ridge 210 into the groove 154 resulting in the configuration shown in FIG. 6.

Figure 6:
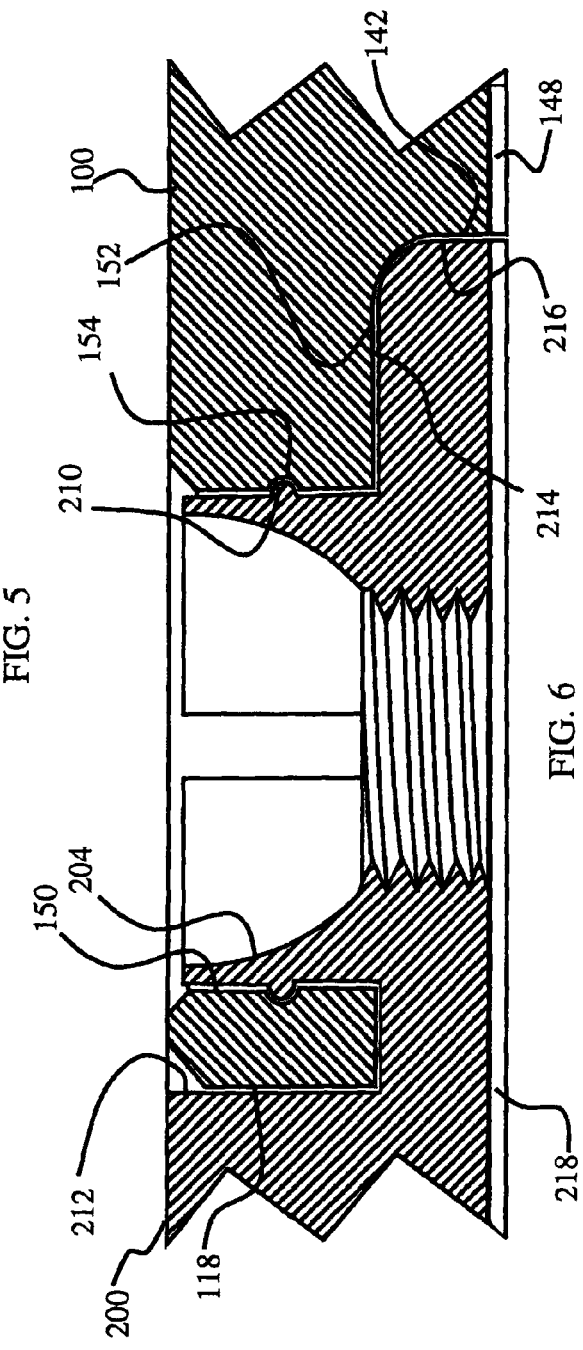
FIG. 6 depicts a partial cross sectional view of the bone plate module of FIG. 1 coupled with the bone plate module of FIG. 4

In FIG. 6, the ridge 210 is located within the groove 154 and the portion of the bone plate module 100 between the bore 150 and the outer perimeter 118 fits within the gap between the taper 204 and the inwardly curved wall 212. Additionally, the overhang 152 rests upon the plateau 214 and the outer perimeter 216 is adjacent to the inwardly curved wall 142. Additionally, the bottom surface 218 of the bone plate module 200 is aligned with the bottom surface 148 of the bone plate module 100. Accordingly since the snap-fit provided in this embodiment results in a rigid connection between the module 100 and the module 200, the combination of the bone plate module 100 and the bone plate module 200 provides a single straight bone plate 156.

Figure 7:
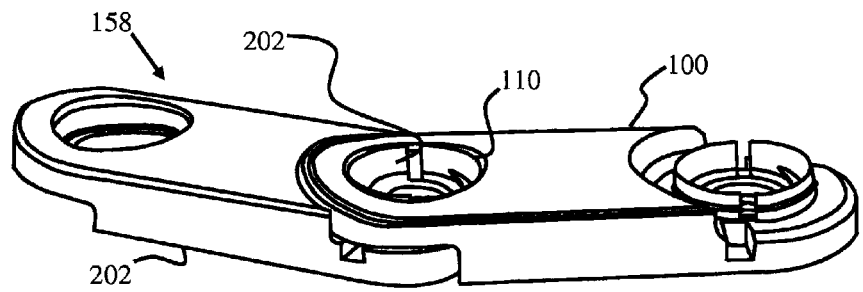
FIG. 7 depicts the bone plate modules of FIG. 4 and FIG. 1 coupled together to form an angled portion of a bone plate.
Figure 8:
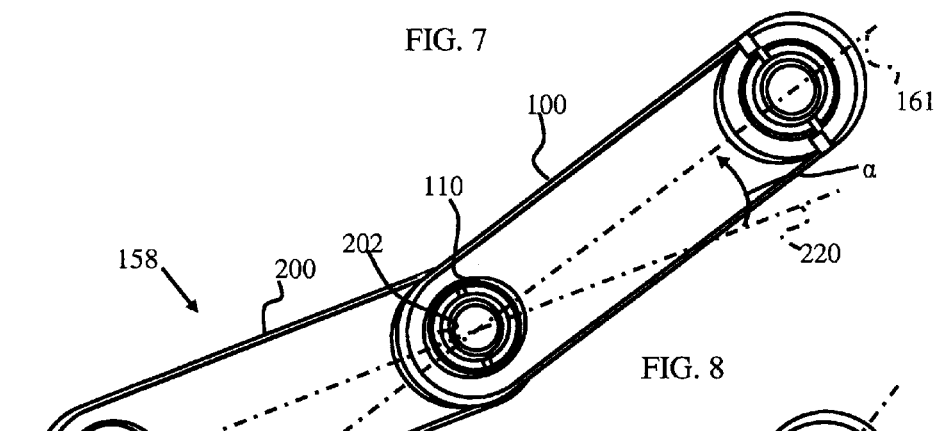
FIG. 8 depicts a top plan view of the angled bone plate modules of FIG. 7.

As described above, the curvature of the inwardly curved wall 146 is complementary to the curvature of the outer perimeter 116 and the curvature of the inwardly curved wall 142 is complementary to the curvature of the outer perimeter 118. Thus, since the bone plate module 200 is identical to the bone plate module 100, the bone plate modules 100 and 200 may be coupled at an angle to each other. As shown in FIGS. 7 and 8, the bone plate modules 100 and 200 may be used to build an angled bone plate 158. This is accomplished by aligning the male coupling portion 202 of the bone plate module 200 with the female coupling portion 110 of the bone plate module 100 such that the longitudinal axis 161 of the plate 100 is set at the angle α with respect to the longitudinal axis 220 of the plate 200 and then pressing the bone plate modules 100 and 200 together in the manner discussed above with respect to the bone plate 156.

Figure 9:
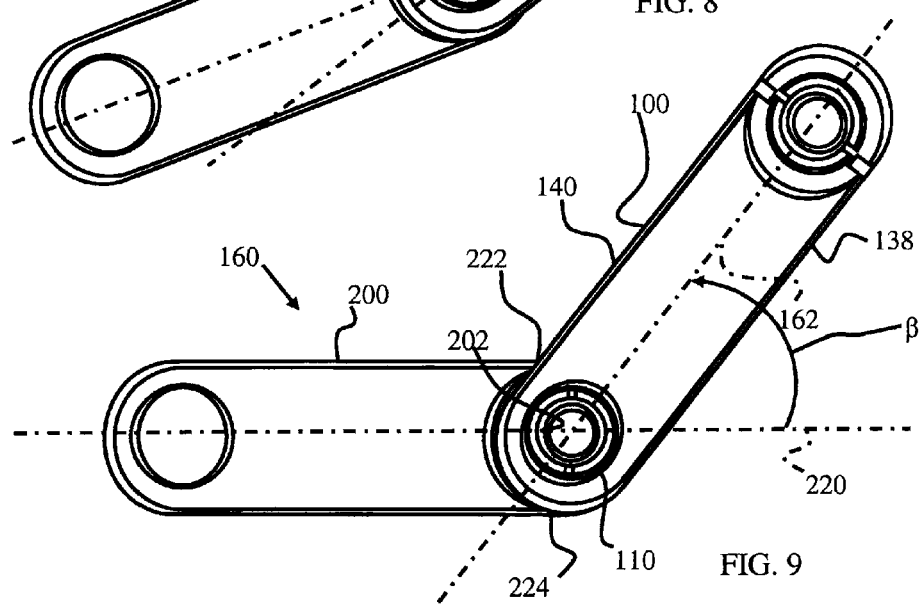
FIG. 9 depicts a top plane view of the bone plate modules of FIG. 4 and FIG. 1 coupled together to form a portion of a bone plate that is angled more than the angled portion shown in FIG. 8.

The bone plate modules 100 and 200 are not constrained to forming a bone plate with a single angle. For example, in the bone plate 160 shown in FIG. 9, the longitudinal axis 162 of the plate 100 is set at an angle β with respect to the longitudinal axis 220 of the plate 200 that is larger than the angle α. The range of angles which can be formed in this embodiment is limited in one direction by the rotation stop 222 which impinges on the side wall 140 and in the other direction by the rotation stop 224 which impinges on the side wall 138.

FIG. 10 shows a bone plate 170 that includes bone plate modules 100 and 200 and a male end cap 178. The bone plate 170 may be fastened to a bone using bone screws 172 and 174. The bone screw 172 is inserted through the taper 120. The head 176 of the bone screw 172 may be threaded to engage the threaded portion 132 of the taper 120. The threaded portion 132 may be triple lead threaded to provide for use of both locking and non-locking screws. A compression screw may be used either with or without a threaded portion 132.

The screw 174 extends through the bore 226. The bore 226, however, has no threads to engage the screw 174. The male end cap 178, however, is threaded as shown in FIG. 11. Specifically, the male end cap 178 includes a male coupling portion 180 with a threaded portion 182 that extends upwardly from a plateau 184. Two notches 186 and 188 are provided in the plateau 184. A base 190 includes a bottom that is formed in like manner to the bottom surface 148 of the bone plate 100.

The base 190 has a curved outer perimeter portion 192 that is substantially identical to the outer perimeter 118 and another curved outer perimeter portion 194 that is complementary to the inwardly curved wall 146. Thus, when the male end cap 178 is installed as shown in FIG. 10, the end portion of the bone plate module 200 is supported as if the bone plate module 200 were coupled with the male coupling portion of another bone plate module. Additionally, the bottom surface of the bone plate 170 provides a uniform contact surface from one end of the plate 170 to the opposites end.

FIG. 12 shows a female end cap 240 that may be used with the bone plate modules 100 and 200. The female end cap 240 includes a female coupling portion 242 with a bore 244 that extends through the female end cap 240. A groove 246 extends around the groove 246. The female end cap 240 has a curved outer perimeter portion 248 that is substantially identical to the outer perimeter 116 and a curved outer perimeter portion 250 that is complementary to the inwardly curved wall 142.

Thus, when the female end cap 240 is installed on the male coupling portion 108, the upper surface of the bone plate 170 provides a uniform upper surface, thereby reducing the potential for irritation to soft tissue adjacent to the plate 170. Additionally, any male coupling portions that are not filled with a screw may be filled, for example, with a threaded plug.

A decoupler 260 is shown in FIGS. 13 and 14 that may be used to be decouple two bone plate modules. The decoupler 260 includes a shaft 262 and a yoke 264. Two stubs 266 and 268 are provided on arms 270 and 272, respectively. The arms 270 and 272 are spaced apart by a distance which is approximately equal to the width of the bone plate module. The stubs 266 and 268 are canted with respect to the shaft 262 and are sized slightly smaller than the notches of the bone plate module with which the decoupler 260 is to be used.

Operation of the decoupler 260 is explained with further reference to FIG. 15. In this example, the decoupler 260 will be used to decouple the bone plate 180 which was formed by coupling the bone plate modules 100 and 200. Initially the decoupler 260 is placed generally perpendicularly to the bone plate module 100 and the yoke 264 moved toward the upper surface 144 of the bone plate module. As noted above, the arms 270 and 272 are separated by about the same distance as the width of the bone plate module 100. Accordingly, the distance between the stubs 266 and 268 is shorter than the width of the bone plate module 100. Therefore, pushing the yoke 264 toward the bone plate module 100 forces the stubs 266 and 268 against the bone plate module 100 causing the arms 270 and 272 to flex apart thereby allowing the stubs 266 and 268 to slide along sidewalls 138 and 140.

As the stubs 266 and 268 approach the notches 114 and 112, the shaft 262 is moved toward a more parallel position with respect to the bone plate module 100. This movement brings the canted stubs 266 and 268 into alignment with the notches 114 and 112. Once aligned the yoke 264 flexes toward its original shape thereby forcing the stubs 266 and 268 into the notches 114 and 112, respectively. The cant of the stubs 266 and 268 with respect to the shaft 262 ensures that the stubs 266 and 268 enter the notches 114 and 112 before the shaft 262 of the decoupler 260 is in contact with the upper surface 144 of the bone plate module 100.

Additionally, the arms 270 and 272 are sized such that as the stubs 266 and 268 enter the notches 114 and 112, the yoke 264 is close to, if not touching, the upper surface 144 of the bone plate module 100. Application of force to the shaft 262 thus causes the yoke 264 to contact the bone plate module 100 and provide a pivot point for the decoupler 260. Pressure on the shaft 262 thus forces the stubs 266 and 268 against the female coupling portion of the bone plate module 200 thereby forcing the groove of the bone plate 200 against the ridge 124 thereby flexing the taper 120 inwardly. As the ridge 124 exits the groove of the bone plate module 200, the bone plate module 200 may be lifter clear of the bone plate module 100.

A kit may include a number of bone plate modules, male end caps, female end caps and a decoupler. Additionally, a template may be provided to assist the surgeon in determining the desired number and orientation of bone plate modules to be used to form a bone plate. In one embodiment, bone plate modules are provided in various lengths. For example, one group of bone plate modules may have a length of about 25 millimeters while a second group has a length of about 30 millimeters, and additional groups may have larger lengths. A bone plate module with a length of about 25 millimeters provides sufficient length to incorporate both a male and a female coupling portion of a size that provides a robust coupling force to obtain a bone plate with the desired rigidity.

FIGS. 16-21 show various bone plate modules that may be provided either separately or in a kit with other bone plate modules. FIG. 16 shows a "Y" shaped bone plate module 300 that includes two female coupling portions 302 located at end portions 304 and 306 and one male coupling portion 308 at an end portion 310. Alternatively, the bone plate module 300 may include two male coupling portions, all female coupling portions or all male coupling portions. A shaft 312 extends between each of the end portions 304, 306 and 310.

The end portions 304 and 306 have the same configuration as the end portion 106 and the end portion 310 has the same configuration as the end portion 104. Likewise, the female coupling portions 302 and the male coupling portion 308 have the same configuration as the female coupling portion 110 and the male coupling portion 108, respectively. Additionally, the shaft 312, at each end portion 304, 306 and 310, has the same configuration as the shaft 102 for the corresponding coupling portion. Thus, since the end portion 310 has a male coupling portion 308 and the end portion 104 of FIG. 1 has a male coupling portion 108, the shaft 312 includes an inwardly curved wall 314 at the end portion 310 that has the same configuration as the inwardly curved wall 142 of FIG. 1.

Accordingly, the bone plate module 300 may be used with the bone plate modules 100 and 200, the male end cap 178 and female end cap 240. Additionally, the decoupler 260 may be used with the bone plate module 300. Finally, the bone plate modules 100, 200 or another bone plate module 300 may be coupled to either of the female coupling portions 302 or the male coupling portion 308 in the same manner that the bone plates 100 and 200 may be coupled together.

Other bone plate modules include the "S" shaped bone plate module 320 of FIG. 17, the "T" shaped bone module 322 of FIG. 18 which is configured with three female coupling portions 324, the "T" shaped bone module 326 of FIG. 19 which is configured with three male coupling portions 328, the curved bone plate module 330 of FIG. 20 and the cross shaped bone plate module 332 of FIG. 21. Each of these bone plate modules, as well as bone plate modules of other shapes, may be configured with various combinations of coupling portions and in various sizes to allow a bone plate to be quickly and easily configured for a particular patient.

While the present invention has been illustrated by the description of exemplary processes and system components, and while the various processes and components have been described in considerable detail, the applicants do not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of the applicants' general inventive concept.

We claim:

1. A method of constructing a bone plate comprising:
   aligning a first male coupling portion of a first bone plate module with a first female coupling portion of a second bone plate module;
   positioning an overhang portion of the second bone plate module relative to a plateau area surrounding the first male coupling portion of the first bone plate module;
   compressing a first taper of the first male coupling portion;
   inserting the compressed first taper into the first female coupling portion;
   rigidly coupling the first bone plate module with the second bone plate module such that the overhang portion surrounds the first male coupling portion;
   placing the rigidly coupled first bone plate module and second bone plate module on a surface of a bone;
   inserting a portion of a first fastener through a second male coupling portion of the second bone plate module; and
   attaching the rigidly coupled first bone plate module and second bone plate module to the surface of the bone with the first fastener.

2. The method of claim 1, further comprising:
   determining a desired angular alignment of the first bone plate module and the second bone plate module;
   placing the first bone plate module at the desired angular alignment with respect to the second bone plate module; and
   maintaining the first bone plate module at the desired angular alignment with the second bone plate module while rigidly coupling the first bone plate module with the second bone plate module.

3. The method of claim 1, further comprising:
   locking the first fastener to the second male coupling portion by engaging a threaded portion of the second male coupling portion with a threaded portion of the first fastener.

4. The method of claim 1, further comprising:
   inserting a ridge of the first male coupling portion into a groove of the first female coupling portion.

5. The method of claim 1, wherein rigidly coupling the first bone plate module with the second bone plate module includes rigidly coupling the first bone plate module with the second bone plate module such that a bottom surface of the second bone plate module is aligned with a bottom surface of the first bone plate module, the bottom surfaces configured to be placed on the surface of the bone.

6. The method of claim 1, further comprising:
   aligning a third male coupling portion of a third bone plate module with a second female coupling portion of the first bone plate module;
   compressing a second taper of the third male coupling portion;
   inserting the compressed second taper into the second female coupling portion;
   rigidly coupling the first bone plate module with the third bone plate module;
   placing the rigidly coupled first bone plate module and third plate module on the surface of the bone;
   inserting a portion of a second fastener through a third female coupling portion of the third bone plate; and
   attaching the rigidly coupled first bone plate module and third plate module to the surface of the bone with the second fastener.

7. The method of claim 1, further comprising:
   aligning a third male coupling portion of a bone plate end cap with a second female coupling portion of the first bone plate module;
   compressing a second taper of the third male coupling portion;
   inserting the compressed second taper into the second female coupling portion; and
   rigidly coupling the first bone plate module with the bone plate end cap.

8. The method of claim 7, wherein rigidly coupling the first bone plate module with the bone plate end cap includes rigidly coupling the first bone plate module with the bone plate end cap such that a bottom surface of the first bone plate module is aligned with a bottom surface of the bone plate end cap, the bottom surfaces configured to be placed on the surface of the bone.

9. The method of claim 1, further comprising positioning a curved outer perimeter of an end of the second bone plate module adjacent the first female coupling portion adjacent to an inwardly curved wall of the first bone plate module adjacent the male coupling portion, wherein a curvature of the outer perimeter of the end of the second bone plate module is complimentary to a curvature of the inwardly curved wall of the first bone plate module.

10. The method of claim 1, wherein the first bone plate module includes a first longitudinal axis, and wherein inserting the compressed first taper into the first female coupling portion includes urging at least one of the first and second bone plate modules in a direction transverse to the first longitudinal axis.

11. A method of constructing a bone plate comprising:
   determining a desired angular alignment of a first bone plate module relative to a second bone plate module;
   positioning the first and second bone plate modules at the desired angular alignment while aligning a first male coupling portion of the first bone plate module with a first female coupling portion of the second bone plate module;
   positioning a recessed area surrounding the first female coupling portion of the second bone plate module relative to a recessed area surrounding the first male coupling portion of the first bone plate module;
   compressing a first taper of the first male coupling portion;
   inserting the compressed first taper into the first female coupling portion;

maintaining the first bone plate module at the desired angular alignment while rigidly coupling the first bone plate module with the second bone plate module;

placing the rigidly coupled first bone plate module and second bone plate module on a surface of a bone;

inserting a portion of a first fastener through a second male coupling portion of the second bone plate module; and attaching the rigidly coupled first bone plate module and second bone plate module to the surface of the bone with the first fastener.

12. The method of claim 11, further comprising:
inserting a portion of a second fastener through a second female coupling portion of the first bone plate module.

13. The method of claim 11, further comprising:
locking the first fastener to the second male coupling portion by engaging a threaded portion of the second male coupling portion with a threaded portion of the first fastener.

14. The method of claim 11, further comprising:
inserting a ridge of the first male coupling portion into a groove of the first female coupling portion.

15. The method of claim 11, wherein rigidly coupling the first bone plate module with the second bone plate module includes rigidly coupling the first bone plate module with the second bone plate module such that a bottom surface of the second bone plate module is aligned with a bottom surface of the first bone plate module, the bottom surfaces configured to be placed on the surface of the bone.

16. The method of claim 11, further comprising:
aligning a third male coupling portion of a third bone plate module with a second female coupling portion of the first bone plate module;

compressing a second taper of the third male coupling portion;

inserting the compressed second taper into the second female coupling portion;

rigidly coupling the first bone plate module with the third bone plate module;

placing the rigidly coupled first bone plate module and third plate module on the surface of the bone;

inserting a portion of a second fastener through a third female coupling portion of the third bone plate; and attaching the rigidly coupled first bone plate module and third plate module to the surface of the bone with the second fastener.

17. The method of claim 11, further comprising:
aligning a third male coupling portion of a first bone plate end cap with a second female coupling portion of the first bone plate module;

compressing a second taper of the third male coupling portion;

inserting the compressed second taper into the second female coupling portion; and rigidly coupling the first bone plate module with the first bone plate end cap.

18. The method of claim 17, wherein rigidly coupling the first bone plate module with the first bone plate end cap includes rigidly coupling the first bone plate module with the first bone plate end cap such that a bottom surface of the first bone plate end cap is aligned with a bottom surface of the first bone plate module, the bottom surfaces configured to be placed on the surface of the bone.

19. The method of claim 17, further comprising:
aligning a third female coupling portion of a second bone plate end cap with a fourth male coupling portion of the second bone plate module;

compressing a third taper of the fourth male coupling portion;

inserting the compressed third taper into the third female coupling portion; and rigidly coupling the second bone plate module with the second bone plate end cap such that a top surface of the second bone plate module is aligned with a top surface of the second bone plate end cap.

20. The method of claim 11, further comprising positioning a curved outer perimeter of an end of the second bone plate module adjacent the first female coupling portion adjacent to an inwardly curved wall of the first bone plate module adjacent the male coupling portion, wherein a curvature of the outer perimeter of the end of the second bone plate module is complimentary to a curvature of the inwardly curved wall of the first bone plate module.

21. The method of claim 11, wherein the first bone plate module includes a first longitudinal axis, and wherein inserting the compressed first taper into the first female coupling portion includes urging at least one of the first and second bone plate modules in a direction transverse to the first longitudinal axis.

22. A method of constructing a bone plate comprising:
determining a first desired angular alignment of a first bone plate module relative to a second bone plate module;

positioning the first and second bone plate modules at the first desired angular alignment while aligning a first male coupling portion of the first bone plate module with a first female coupling portion of the second bone plate module;

determining a second desired angular alignment of the first bone plate module relative to the second bone plate module, the second desired angular alignment different than the first desired angular alignment;

positioning the first and second bone plate modules at the second desired angular alignment while aligning the first male coupling portion of the first bone plate module with the first female coupling portion of the second bone plate module;

compressing a first taper of the first male coupling portion;

inserting the compressed first taper into the first female coupling portion such that a ridge of the first male coupling portion is received into a groove of the first female coupling portion;

maintaining the first bone plate module at the desired angular alignment while rigidly coupling the first bone plate module with the second bone plate module such that a bottom surface of the first bone plate module is aligned with a bottom surface of the second bone plate module;

placing the rigidly coupled first bone plate module and second bone plate module on a surface of a bone such that the bottom surfaces of the bone plate modules are placed on the surface of the bone;

inserting a portion of a first fastener through a second male coupling portion of the second bone plate module;

locking the first fastener to the second male coupling portion by engaging a threaded portion of the second male coupling portion with a threaded portion of the first fastener; and attaching the rigidly coupled first bone plate module and second bone plate module to the surface of the bone with the first fastener.

* * * * *